United States Patent [19]
Horrobin et al.

[11] Patent Number: 5,318,991
[45] Date of Patent: Jun. 7, 1994

[54] FATTY ACID TREATMENT TO REDUCE CALCIUM EXCRETION

[75] Inventors: David F. Horrobin, Guildford, England; Alfred C. Buck, Glasgow, Scotland

[73] Assignee: Efamol Holdings PLC, Surrey, England

[21] Appl. No.: 51,436

[22] Filed: Apr. 22, 1993

Related U.S. Application Data

[62] Division of Ser. No. 892,814, Jun. 5, 1992, abandoned.

[30] Foreign Application Priority Data

Jun. 5, 1991 [GB] United Kingdom ............... 9112052

[51] Int. Cl.$^5$ ............................................. A61K 31/20
[52] U.S. Cl. ........................................ 514/560; 514/558
[58] Field of Search ................................ 514/560, 558

[56] References Cited

U.S. PATENT DOCUMENTS 4,816,483 3/1989 Georgieva et al. ................. 514/558
4,855,136 8/1989 Horrobin et al. .................. 424/602
5,116,624 5/1992 Horrobin et al. .................. 424/702

FOREIGN PATENT DOCUMENTS 0261814 3/1988 European Pat. Off. .
1417119 12/1975 United Kingdom .

OTHER PUBLICATIONS

Patent Abstracts of Japan vol. 13, No. 419 (C-637) [3767], Sep. 1989 & JP-A-1 157 912 (Nippon Oil & Fats Co., Ltd.) Jun. 1989.

*Primary Examiner*—Frederick E. Waddell
*Assistant Examiner*—T. J. Criares
*Attorney, Agent, or Firm*—Nixon & Vanderhye

[57] ABSTRACT

Reduction of urinary calcium excretion in humans or animals by the administration of GLA or DGLA as much or in salt or other pharmacologically acceptable form, optionally in association with EPA, DHA or other EFA in similar forms, is also useful in the treatment of nephrocalcinosis, renal stones and osteoporosis.

11 Claims, No Drawings

FATTY ACID TREATMENT TO REDUCE CALCIUM EXCRETION

This is a division of application Ser. No. 07/892,814, filed Jun. 5, 1992, now abandoned.

FIELD OF INVENTION

This invention relates to fatty acid treatments, and in particular to reduction of urinary calcium excretion, and more particularly to treatment of osteoporosis.

FATTY ACIDS

The pathways of conversion of the main series of polyunsaturated fatty acids in the body are as in Table 1 below:

TABLE 1

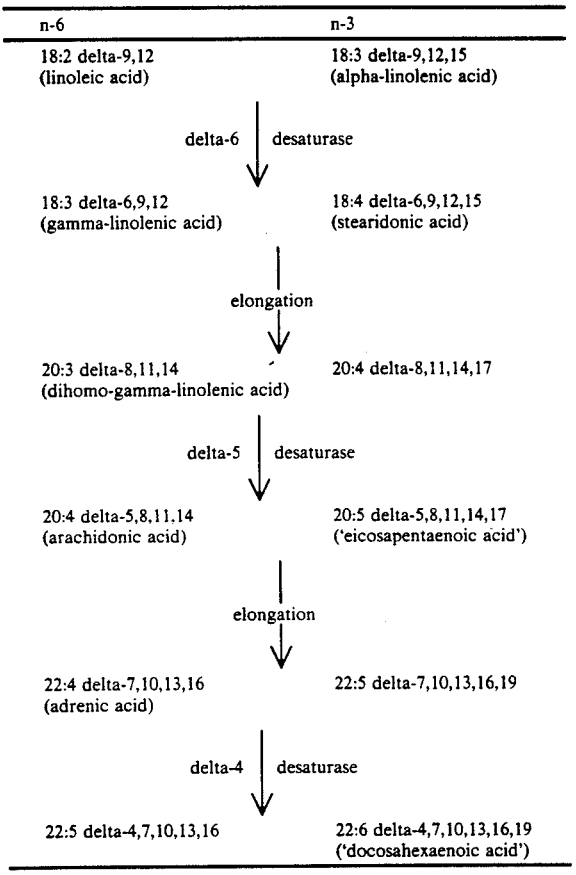

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids, e.g. delta-9,12-octadecadienoic acid or delta-4,7,10,13,16,19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alphaacid.

CALCIUM EXCRETION, DISCUSSION AND EXPERIMENTAL

Excretion of calcium in the urine of humans and of animals is significant for at least two reasons:
1. High levels of calcium in the urine may lead to crystals of calcium salts being precipitated leading to the development of renal and urinary tract stones with consequent damage to the kidneys, urinary tract and bladder,
2. Calcium is reqyired for nornal bone strength and loss of calcium in the urine can contribute to weakening of the bones and the development of osteoporosis, a major medical problem.

We have recently discovered a new and safe way of reducing calcium excretion by the administration of gamma-linolenic acid (GLA). As discussed above, GLA is the first metabolite of linoleic acid, the major essential fatty acid in the diet. Linoleic acid is converted to GLA by the enzyme delta-6-desaturase. However, this step is slow and rate limiting even in the normal body and as a result there are advantages in the administration of GLA directly.

In the following discussion, percentages are by weight unless otherwise stated.

Calcium excretion is increased in diabetic animals and humans and so the use of diabetic animals provides a useful model for the investigation of calcium excretion. Sixteen adult rats, weighing in the range of 140 to 160 g (all males), were used in the experiments. They were divided into two groups of eight and treated as follows:
i. Fed ordinary laboratory chow for one week. At the end of the week each animal was put in a metabolic cage for twenty four hours, all its urine collected, and the calcium content of the urine measured by atomic absorption spectrophotometry.
ii. Fed on laboratory chow supplemented with 10% safflower oil (eight animals) or evening primrose oil (eight animals) for two weeks. Again at the end of the period twenty four hour urinary calcium excretion was measured.
iii. All animals were then treated with streptozotocin, a chemical which damages the islets of Langerhans in the pancreas and makes the animal diabetic. After two further weeks, during which the animals continued to receive either safflower oil or evening primrose oil, twenty four hour urinary calcium was again measured.

Evening primrose oil (EPO) and safflower oil (SFO) are very similar in being exceptionally rich in essential fatty acids, but they differ in one important respect. Safflower oil contains about 82% linoleic acid but no GLA. EPO contains about 72% linoleic acid and 9% GLA. Thus differences between the actions of safflower oil and EPO can be attributed to GLA.

The results are shown in the table (twenty four hour calcium, mmol, means±SD)

|  | Chow only | Chow + oil | Diabetes, chow + oil |
|---|---|---|---|
| SFO group | 19.6 ± 4.3 | 17.9 ± 3.7 | 79.2 ± 17.4 |

|  | Chow only | Chow + oil | Diabetes, chow + oil |
| --- | --- | --- | --- |
| EPO group | 20.2 ± 3.4 | 12.3 ± 2.3 | 31.1 ± 8.4 |

The results show clearly that SFO in the prediabetic animals had no effect on calcium excretion and that as expected, diabetes produced a very substantial rise in calcium excretion. EPO, even in the prediabetic animals, reduced calcium excretion. Further although in the EPO group calcium excretion increased when they were made diabetic, this increase was much less than in the SFO group.

An additional study was conducted to investigate the effect of omega-6 and omega-3 fatty acids on nephrocalcinosis in rats. Adult rats in groups of n animals were used in this experiment divided as detailed below:

i) Fed ordinary laboratory chow for 24 days. Renal tissue calcium content was analysed on sacrifice at 24 days.
ii) Fed ordinary laboratory chow for 24 days and having calcium gluconate i.p. (intraperitoneal injection) from days 15 to 24 inclusive. Assessments made as in i).
iii) Fed laboratory chow containing 1% evening primrose oil (EPO) for 24 days and having calcium gluconate i.p. from days 15 to 24 inclusive. Assessments made as in i) above.
iv) Fed laboratory chow containing 1% evening primrose oil/1% cold water marine fish oil containing 18% EPA and 12% DHA for 24 days and having calcium gluconate i.p. from days 15 to 24 inclusive. Assessments made as in i) above.

Results of the study are summarised below:

|  | Renal Tissue Calcium mg/g d 24 |
| --- | --- |
| Control (n = 6) | 74.0 ± 5.4 |
| Control + Ca Gluconate (n = 6) | 938 ± 581 |
| 1% EPO + Ca Gluconate (n = 6) | 350 ± 125 |
| 1% EPO/1% fish oil + Ca Gluconate (n = 6) | 321 + 161 |

It can be seen that both EPO and EPO/fish oil have the ability to reduce renal tissue calcium levels significantly even after exaggeration of calcium levels following continuous calcium gluconate i.p. injections. The effect of combination of EPO/fish oil is greater than that of EPO alone.

A further study investigated the effects of both EPO & EPO/fish oil in combination on hypercalciuria induced by injection of streptozotocin in rats. The action of streptozotocin has been previously explained. Adult rats were used in this experiment and were divided into groups as detailed below:

i) Fed standard laboratory chow for 18 days.
ii) Injected with streptozotocin at day zero and fed standard laboratory chow for 18 days.
iii) Injected with streptozotocin at day zero and fed standard laboratory chow having 1% EPO added for 18 days.
iv) Injected with streptozotocin at day zero and fed standard laboratory chow having 1% EPO/1% fish oil added for 18 days.

Urine calcium excretion was measured at baseline and the results converted into calcium:creatinine ratios which are summarised below:

|  | Baseline | Day 18 |
| --- | --- | --- |
| Control (n = 6) | 0.30 ± 0.32 | 0.69 ± 0.32 |
| Control + STZ (n = 6) | 0.99 ± 1.05 | 3.61 ± 1.11 |
| STZ + EPO (n = 6) | 0.28 ± 0.26 | 2.24 ± 1.50 |
| STZ + EPO/fish oil (n = 6) | 0.67 ± 0.70 | 1.35 ± 1.19 |

These results show that both EPO alone and EPO/fish oil reduced the hypercalciuria observed at day 18 but the latter had a considerably greater effect.

As a result of these studies we set up an investigation in patients with both high urinary calcium excretion (hypercalciuric baseline calcium >6.5 m mole/liter, and normal urinary calcium excretion (normocalciuric) all of whom had experienced recurrent formation of urinary calcium-containing stones. A group of normal individuals was also included as controls.

Because it was felt from previous animal data that a combination of omega-6 and omega-3 fatty acids would have the optimal effect on reducing urinary calcium excretion all groups were first given placebo oil capsules per day for 4 weeks followed by 8 capsules per day of a combination of evening primrose oil and cold-water marine fish oil providing 782 mg GLA, 159 mg EPA and 106 mg DHA every day. Then 24 hour urinary calcium measurements were made at baseline, after 4 weeks placebo and after 4 weeks active treatment and compared. Results are summarised below:

|  | Mean 24 hour Urine Calcium | | | |
| --- | --- | --- | --- | --- |
|  | Baseline | Placebo 4 weeks | Active 4 weeks | Probability Placebo/Active Difference |
| Hypercalciuric stone formers (n = 15) | 9.23 ± 2.91 | 8.77 ± 2.86 | 6.74 ± 1.99 | <0.05 |
| Normocalciuric stone formers (n = 15) | 4.31 ± 1.39 | 4.87 ± 2.39 | 3.68 ± 1.91 | ns |
| Normal controls (n = 15) | 3.55 ± 2.11 | 3.83 ± 2.14 | 2.60 ± 1.25 | <0.05 |

It is evident that a combination of EPO and fish oil can significantly reduce urinary calcium excretion whereas administration of a placebo cannot. The effect is most marked in hypercalciuric stone formers. It is also present in normal controls and present but not significant in normocalciuric stone formers. In the last group a larger number of patients would probably show a significant effect.

THE INVENTION

Based on the above, the invention in one aspect lies in the use of GLA and/or its immediate and rapidly produced metabolite DGLA, for the preparation of a medicament for the reduction of urinary calcium excretion.

Alternatively, the invention may be regarded as lying in a method of reduction of urinary calcium excretion wherein an effective daily amount of GLA or DGLA is administered in any convenient form to animals or humans suffering from or at risk of an undue level of such excretion, with the desirable result of preventing renal stone formation, nephrocalcinosis and osteoporosis.

In other aspects, whether of the use of GLA and/or DGLA in preparation of medicaments or in treatment as above, the invention correspondingly concerns treatment or prevention of osteoporosis and/or treatment or prevention of development of nephrocalcinosis and/or renal stones in either animals or humans.

As noted, GLA in the body is very rapidly converted to dihomo-gamma-linolenic acid (DGLA); DGLA therefore has a very similar effect to GLA.

As discussed further below GLA or DGLA may be used in any appropriate form, including but not limited to triglyceride, diglyceride, monoglyceride, free fatty acid, any appropriate ester, any appropriate salt including the lithium, sodium, potassium, calcium, zinc, magnesium or other salt, phospholipid, amide or any other pharmacologically acceptable form.

The preferred dose range is 0.01 to 1000 mg/kg/day, more preferably 0.5 to 50 mg/kg/day, very preferably 2 to 30 mg/kg/day of GLA or DGLA, and medicaments are readily prepared in dosage unit form to administer such amounts (related to a 70 kg human adult). The calcium salts would be particularly appropriate for the treatment of osteoporosis since they would provide calcium at the same time as reducing calcium excretion. They would, of course, not be appropriate for the treatment of patients with renal stones where calcium supply to the patient should be reduced.

The GLA or DGLA may be used with any essential fatty acids of the n-6 or n-3 group, including, for example, arachidonic acid, alpha-linolenic acid, eicosapentaenoic acid or docosahexaenoic acid, in like doses. In particular, in view of results on human calcium excretion, GLA in combination with EPA and/or DHA is desirable, producing particularly advantageous effects.

ROUTES OF ADMINISTRATION

Oral, parenteral (sub-cutaneous, intramuscular, intravenous or by any other appropriate route), enteral, topical in the form of appropriate GLA-containing ointments, creams, lotions, patches, etc. vaginal or rectal are among suitable routes of administration.

DERIVATIVES OF EFAs

As indicated above, the acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect indentification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform;methanol (2:1). The extract is filtered through solium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of methods of treatment and in the use of GLA or DGLA in the preparation of pharmaceutical compositions, but it will be understood that the gamma-linolenic and other EFAs, being in the nature of dietary supplements, can be incorporated in a dietary margarine or other foodstuff and such are to be understood as within the term pharmaceutical composition or medicament herein (including in the claims) when for the purposes set out.

If desired, pharmaceutical compositions may be produced for use in the invention by associating the natural or synthetic acids, as such or as derivatives, with an acceptable pharmaceutical vehicle. It is, however, at present convenient to provide at least GLA in the form of an available oil having a high GLA content, hence reference to "oils" herein.

One source of oils currently available is the seed of evening primrose species such as *Oenothera biennis L.* and *Cenothera lamarckiana*, the oil extract therefrom containing about 8% GLA and about 72% linoleic acid in the form of their glycerides, together with other glycerides (percentages based on total fatty acids). Other sources of GLA are borage species such as *Borago officinalis* which provide a richer source than Oenothera oil. Oils from the seeds of members of the Ribes family are also often rich in GLA. Recent studies on fungi which can be cultivated by fermentation promise a fungal oil source. Some algae also produce GLA & may be harvested or cultured. Synthesis is also possible.

The oil is extracted from the seed by one of the conventional methods of extraction such as cold pressure, screw pressure after partially cooking the seed, or solvent extraction.

Fractionation of a typical sample of evening primrose oil as used in the work reported herein in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gammalinolenic and linoleic acids as the main fatty acid components, the gamma-linolenic acid content being, if desired, a major proportion. Seed oil extracts appear to have a stabilising effect upon DGLA if present.

SOURCES OF OTHER ACIDS

DGLA can be prepared by chemical synthesis or by fungal fermentation. For the higher n-6 acids, natural sources of 22:4 and 22:5 n-6 acids include adrenal glands (22:5) and kidneys (22:4) obtained from slaughter houses, which also give AA sources.

The n-3 acids have long been available from marine oils, particularly the 20:5 n-3 (EPA) and 22:6 n-3 (DHA) acids, and more recently from microbial and algal fermentation. They can be isolated from these sources by, for example, saponification under mild non-oxidising conditions followed by preparative gas liquid chromatography. Synthesis is difficult but not impossible and provides another source.

PHARMACEUTICAL PRESENTATION

As mentioned briefly above, the compositions are conveniently in a form suitable for oral, topical, parenteral or other route of administration in a suitable pharmaceutical vehicle, as discussed in detail, for example, in Williams British Patent Specification No. 1 082 624 to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera or other oil may be prepared using albumin to solubilise the free acid. Emulsions and salts can also be administered by infusion or injection.

Advantageously, a preservative is incorporated into the preparation. Alphatocopherol in concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed by on the other hand should also desirably be adequate to allow the desired rate of administration to be achieved by a small number of doses. The rate of administration will moreover depend on the precise pharmacological action desired.

EXAMPLES

The following are examples of compositions and their administration for the purposes discussed herein.

1. Administration of 100 mg to 2000 mg of GLA per day in the form of soft or hard gelatin capsules or tablets providing:
   a. 40 to 80 mg per capsule of GLA in the form of evening primrose oil.
   b. 50-150 mg per capsule of GLA in the form of borage, blackcurrant, fungal or other appropriate oil.
   c. 100-500 mg GLA per capsule in the form of triglyceride GLA, or any appropriate salt of GLA, such as the lithium or calcium or magnesium or zinc or potassium salts.

2. Administration of DGLA in a dose of 100 mg to 2000 mg per day in the forms of 1c above.

3. Administration of GLA or DGLA in association with EPA, with or without DHA, for example as a 40 to 80 mg GLA per capsule in the form of evening primrose oil together with 10 mg to 100 mg per capsule of EPA in the form of cold water marine fish oil.

4. Administration of GLA or DGLA in the form of a soluble powder or effervescent granule formed from any appropriate salt of GLA as in 1 c above and excipients such as citric acid monohydrate, sodium bicarbonate or other dibasic acids such as tartaric or maleic acid plus sweeteners such as sucrose or sorbitol and flavourings.

5. Administration of GLA or DGLA in the form of liquid evening primrose, borage or other appropriate oil as the oil itself or as a whip or emulsion prepared with appropriate flavours and stabilizers known to those skilled in the art.

6. Administration of GLA or DGLA in any appropriate chemical form, microencapsulated using starch, gelatin, gum arabic or other appropriate formulation known to those skilled in the art.

7. Administration of GLA in the form of pressaries, suppositories, skin patches or any other appropriate route.

8. Calcium-GLA tablets or soft or hard gelatin capsules containing 500 mg of calcium-GLA salt to be taken 1-5 times/day.

We claim:

1. A method of reducing urinary calcium excretion in humans or animals by administering to a human or animal in need of same an effective amount of a fatty acid selected from the group consisting of gamma-linolenic acid, dihomo-gamma-linolenic acid and both, as such or as a salt of a pharmacologically acceptable form.

2. The method according to claim 1, wherein there is also administered a fatty acid selected from the group consisting of eicosapentaenoic acid, docosahexaenoic acid, arachidonic acid, alpha-linolenic acid and mixtures thereof as such or as a salt or a pharmacologically acceptable form.

3. The method according to claim 2 in which the salt is calcium.

4. The method according to claim 1, wherein the amount of gamma-linolenic acid or dihomo-gamma-linolenic acid or their mixture administered is from 0.1 to 1,000 mg/kg/day.

5. The method according to claim 4, wherein the amount of gamma-linolenic acid or dihomo-gamma-linolenic acid or their mixture administered is from 0.5 to 50 mg/kg/day.

6. The method according to claim 5, wherein the amount of gamma-linolenic acid or dihomo-gamma-linolenic acid or their mixture administered is from 2 to 30 mg/kg/day.

7. The method according to claim 2, wherein the amount of eicosapentaenoic acid, docosahexaenoic acid, arachidonic acid, alpha-linolenic acid or mixtures thereof administered is from 0.1 to 1,000 mg/kg/day.

8. The method according to claim 7, wherein the amount of eicosapentaenoic acid, docosahexaenoic acid, arachidonic acid, alpha-linolenic acid or mixtures thereof administered is from 0.5 to 50 mg/kg/day.

9. The method according to claim 8, wherein the amount of eicosapentaenoic acid, docosahexaenoic acid, arachidonic acid, alpha-linolenic acid or mixtures thereof administered is from 2 to 30 mg/kg/day.

10. The method according to claim 1, wherein the fatty acid is administered in unit dosage form.

11. The method according to claim 2, wherein the fatty is administered in unit dosage form.

* * * * *